US008853619B2

(12) United States Patent
Preudhomme et al.

(10) Patent No.: US 8,853,619 B2
(45) Date of Patent: Oct. 7, 2014

(54) METHOD FOR DETECTING TRACER COMPOUNDS FOR HYDROCARBON PRODUCTION

(75) Inventors: Hugues Preudhomme, Lons (FR); Coralie Serres Piole, Pau (FR); Annie Commarieu, Pau (FR); Fabrice Aubertin, Limendous (FR)

(73) Assignee: Total S.A., Courbevoie (FR)

( * ) Notice: Subject to any disclaimer, the term of this patent is extended or adjusted under 35 U.S.C. 154(b) by 80 days.

(21) Appl. No.: 13/094,411

(22) Filed: Apr. 26, 2011

(65) Prior Publication Data

US 2011/0260051 A1 Oct. 27, 2011

(30) Foreign Application Priority Data

Apr. 27, 2010 (FR) ...................................... 10 53203

(51) Int. Cl.
| | | |
|---|---|---|
| H01J 49/00 | (2006.01) | |
| E21B 43/16 | (2006.01) | |
| E21B 47/10 | (2012.01) | |
| G01N 30/88 | (2006.01) | |

(52) U.S. Cl.
CPC .... *E21B 47/1015* (2013.01); *G01N 2030/8854* (2013.01); *E21B 43/16* (2013.01)
USPC ............................ 250/281; 250/282; 250/301

(58) Field of Classification Search
CPC ............ E21B 47/1015; Y10S 507/907; Y10S 507/924
USPC .......................... 250/281, 282, 288, 301, 304
See application file for complete search history.

(56) References Cited

U.S. PATENT DOCUMENTS

| | | |
|---|---|---|
| 5,246,860 A | 9/1993 | Hutchins |
| 2003/0006036 A1 | 1/2003 | Malone et al. |
| 2006/0144588 A1 | 7/2006 | Ferguson et al. |
| 2007/0215385 A1 | 9/2007 | Anderson |

FOREIGN PATENT DOCUMENTS

| | | |
|---|---|---|
| WO | WO 02/095189 A1 | 11/2002 |
| WO | WO 2006/047478 A2 | 5/2006 |
| WO | WO 2009/070233 A1 | 6/2009 |

OTHER PUBLICATIONS

United Kingdom Search Report for corresponding Application No. GB1107114.9.
French Search Report (EPO Form 1503 12.99 (P04014)), from corresponding French Application No. 10/53203 (3 pages).
Anonymous, "High-Performance Liquid Chromatography" (online) pp. 1-9, URL: http://en.wikipedia.org/wiki/High_performance_liquid_chromatography, (downloaded Dec. 10, 2010).
Coralie Serres-Piole, et al., "UPLC-ICPMS/ESIMSMS: un couple universel & seduisant pour le suivi a haut debit d'empreintes moleculaires de metabolites bio-inorganiques dans des fluides biologiques", CNRS, Sep. 21, 2009 (21 pages).
Michael E. Swartz, Ph.D., "Ultra Performance Liquid Chromatography (UPLC): An Introduction", Separation Science Redefined, May 2005, pp. 8-14.

*Primary Examiner* — Nicole Ippolito
*Assistant Examiner* — Hanway Chang
(74) *Attorney, Agent, or Firm* — Marsh Fischmann & Breyfogle LLP

(57) ABSTRACT

The invention concerns a method for surveying a subsurface formation containing hydrocarbons, comprising:
injecting at least one tracer compound into the subsurface formation;
recovering a fluid derived from the subsurface formation;
detecting the tracer compound in the fluid by liquid chromatography analysis coupled with tandem mass spectrometry analysis, the liquid chromatography analysis being conducted with a stationary phase composed of particles having a mean size equal to or less than 2.1 μm.

18 Claims, No Drawings

METHOD FOR DETECTING TRACER COMPOUNDS FOR HYDROCARBON PRODUCTION

FIELD OF THE INVENTION

The present invention concern a method for the improved detection of tracer compounds injected into a subsurface formation for hydrocarbon production, which is based on analysis using ultra-high performance liquid chromatography coupled with tandem mass spectrometry analysis.

TECHNICAL BACKGROUND

For the production of hydrocarbons contained in a subsurface formation, often less than one half of the existing hydrocarbons are recovered by primary means i.e. using the natural pressure of the gas or liquids contained in the subsurface formation. To complete primary recovery, secondary recovery can be performed in which production comprises the injection of water optionally with the addition of synthetic or natural molecules (polymers, alkalis, surfactant compounds . . .).

To optimize the recovery of hydrocarbons it is possible to conduct tracer campaigns of the reservoir. Tracers are added to the injected fluid (water or gas). The fluid travels through the reservoir. The tracers are produced together with the producted fluid (water, gas). Measurement of the time separating the injection of a tracer compound and its arrival at the production point allows the determination, inter alia, of the scanned volume of the reservoir. This is of importance when assessing expected production rates and for determining the quantity of water and/or chemical additives to be injected into the subsurface formation.

The injection of a plurality of tracer compounds allows the conducting of simultaneous analyses (for example when several injection wells are used) or of successive tracer tests over time. The changes in the quantity of different tracer compounds recovered as a function of time or of the volume of producted fluid can therefore be used to obtain a complete mapping of the flows in the subsurface formation, and for example to detect flow aberrations due to pressure differentials in the subsurface formation which may distort performance levels.

Documents U.S. Pat. No. 5,246,860, WO 02/095189 and WO 2006/047478 provide examples of methods for marking injection fluids.

At the current time, the method which is most often used is gas chromatography associated with mass spectrometry (which may or may not be tandem). However this method is very cumbersome to implement. In particular it requires a complex preparation of the samples, with a chemical derivatization of the tracer compounds necessary to transform them into gas form. Part of the tracer compounds is lost during this step. In addition, the analysis itself is time-consuming (about 60 minutes).

There is therefore a true need to provide a novel detection and analysis method for tracer compounds that is simpler, quicker and preferably having more or less the same efficiency as current methods in particular gas chromatography coupled with mass spectrometry.

SUMMARY OF THE INVENTION

The invention first relates to a method for surveying a subsurface formation containing hydrocarbons, which comprises:

injecting at least one tracer compound into the subsurface formation;
recovering a fluid derived from the subsurface formation;
detecting the tracer compound in the fluid by liquid chromatography analysis coupled with tandem mass spectrometry analysis, the analysis by liquid chromatography being conducted with a stationary phase composed of particles having a mean size of 2.1 μm or less.

According to one embodiment, the method comprises the injection of a plurality of different tracer compounds into the subsurface formation, the recovery of one of more fluids derived from the subsurface formation and the detection of each tracer compound in the fluid or fluids by liquid chromatography analysis coupled with tandem mass spectrometry analysis, the liquid chromatography analysis being conducted with a stationary phase composed of particles having a mean size equal to or less than 2.1 μm.

According to one embodiment, the tracer compound(s) are selected from the derivative compounds of naphthalene sulphonic acid and the halogenated compounds derived from benzoic acid.

According to one embodiment, at least part of the tracer compounds are selected from the derivatives of benzoic acid whose aromatic ring comprises one fluorine substituent, two fluorine substituents, three fluorine substituents, four fluorine substituents, one trifluoromethyl substituent or two trifluoromethyl substituents.

According to one embodiment, at least one part of the tracer compounds are compounds of formula:

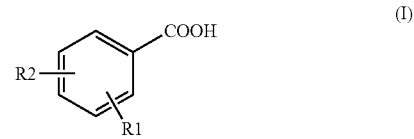

(I)

wherein R1 and R2 represent two substituents different from one another, selected from F, Cl, Br and CF$_3$.

According to one embodiment, at least one part of the tracer compounds are selected from 2-chloro-4-fluorobenzoic acid, 2-chloro-6-fluorobenzoic acid, 3-chloro-2-fluorobenzoic acid, 3-chloro-4-fluorobenzoic acid, 4-chloro-2-fluorobenzoic acid, 5-chloro-2-fluorobenzoic acid, 2-fluoro-3-(trifluoromethyl)benzoic acid, 2-fluoro-4-(trifluoromethyl)benzoic acid, 2-fluoro-5-(trifluoromethyl)benzoic acid, 2-fluoro-6-(trifluoromethyl)benzoic acid, 3-fluoro-4-(trifluoromethyl)benzoic acid, 3-fluoro-5-(trifluoromethyl)benzoic acid, 4-fluoro-2-(trifluoromethyl)benzoic acid, 4-fluoro-3-(trifluoromethyl)benzoic acid and 5-fluoro-2-(trifluoromethyl)benzoic acid.

According to one embodiment, the tracer compound or compounds are injected into the subsurface formation via one or more injection wells, in the form of one or more aqueous solutions, and the fluid or fluids emerging from the subsurface formation comprise water and hydrocarbons and are recovered in one or more production wells.

According to one embodiment, the detection of the tracer compound in the fluid or fluids comprises:
taking a sample of fluid;
optionally treating the fluid sample by solid phase extraction;
filtering the sample;
determining the presence of absence of the tracer compound(s) in the sample, and optionally measuring the quantity of tracer compound(s) present in the sample.

According to one embodiment, the solid phase extraction is conducted on a support having hydrophilic and hydrophobic functions, and preferably a macroporous poly(divinylbenzene-co-N-vinylpyrrolidone) copolymer support.

According to one embodiment, the solid phase extraction is conducted by treatment of the support with at least one treatment solution, by loading the sample, by washing the support with at least one washing solution and by eluting with at least one eluting solution, the treatment, washing and eluting solutions preferably being mixtures of acetonitrile and water.

With the present invention it is possible to overcome the disadvantages of the prior art. In particular it provides a novel method for detecting and analyzing tracer compounds that is simpler, quicker and most of the time practically just as efficient (or at least just as efficient) as current methods in particular gas chromatography (coupled with mass spectrometry).

This is obtained through the use of ultra-high performance liquid chromatography (UPLC), i.e. using a stationary phase made of particles of small size and operating at high pressure (typically of the order of 1000 bar), coupled with tandem mass spectrometry.

According to some particular embodiments, the invention also has one or preferably several of the advantageous characteristics listed below:

- The method of the invention is quicker and simpler to carry out than techniques based on gas chromatography. The working time required is considerably shortened (a total of about 30 minutes compared with more than one day for gas chromatography). In addition, losses of some tracer compounds are avoided, such as 3,5-bis(trimethylfluoro)benzoic acid.
- It is possible to apply the method of the invention without any prior preparation of the samples, aside from filtration.
- It is also possible to prepare the samples of production fluid, prior to analysis and in a particularly fast and efficient manner, by performing solid phase extraction in a single step to lower the limits of detection and quantification.
- Compared with detection using conventional liquid chromatography (i.e. whose stationary phase comprises particles having a typical size of 5 μm), the method of the invention allows much lower quantification limits to be achieved (of the order of $10^{-9}$ g/g or less, instead of typically $10^{-7}$ g/g).
- The method can be applied with all known tracer compounds, in particular known fluorinated derivatives of benzoic acid, or naphthalene sulphonic acids. It can also be used with additional tracer compounds such as other halogenated derivatives of benzoic acid, which allows more detailed, more complex analysis of the characteristics of the subsurface formation, by means of a larger set of tracer compounds.

DESCRIPTION OF EMBODIMENTS OF THE INVENTION

The invention will now be described in more detail and in non-limiting manner in the following description.

Injection, Recovery and Detection of Tracer Compounds

The invention proposes the use of tracer compounds for characterizing (or surveying, examining, analyzing, monitoring) a subsurface formation containing hydrocarbons, with a view to optimizing hydrocarbon production by means of a better understanding of the structure of the formation and of the flow of fluids in this reservoir.

At least one tracer compound is injected into the subsurface formation. Preferably several tracer compounds are injected into the subsurface formation to conduct a more complete survey.

Preferably, the tracer compound or compounds are injected in the form of aqueous solutions into one or more injection wells. When some water (to which additives are optionally added) is injected into the subsurface formation to improve hydrocarbon recovery, the tracer compound(s) may simply be dissolved in the injection water on site, or they may be added to the injection water in the form of a concentrated solution which is diluted in the injection water on site.

Preferably, the tracer compounds are present in the aqueous solutions at concentrations of 20 weight % or less.

One or more fluids derived from the subsurface formation, which may contain the tracer compounds are recovered. In general, these fluids are production fluids recovered from one or more production wells. These fluids may be liquid/gas mixtures and may possibly contain solid particles. In particular, they may contain water and hydrocarbons. One or more samples are taken of the fluid or fluids. These samples are optionally stripped of their gas fraction and/or their solid fraction and optionally stripped of an oil fraction (so as only to retain an essentially aqueous fraction). The detection of the tracer compound or compounds in the samples is then conducted to determine whether the tracer compounds are present in the samples, and optionally to identify those tracer compounds present and to determine the concentration thereof.

The detection of tracer compounds is based on liquid chromatography analysis followed by tandem mass spectrometry. Tandem mass spectrometry allows the characterization/determination of the compounds according to their empirical formula, and chromatography allows differentiation of the isomer compounds.

No derivatization step of the tracer compounds is necessary with the invention.

The liquid chromatography used is so-called UPLC chromatography. It is characterized by the use of a stationary phase having small-sized particles, and operates at high pressure (typically of the order of 1000 bar).

More precisely, the mean size of the stationary phase particles is preferably equal to or less than 2.1 μm (compared with typically about 5 μm for conventional type liquid chromatography). The mean particle size is defined in the present application as the Dv50 of the particles, i.e. the $50^{th}$ percentile of particle size distribution. In other words, 50% of the particles have a size equal to or less than Dv50 and 50% have a size equal to or more than Dv50. The Dv50 is characteristic of the particle size distribution (volumetric distribution) of the stationary phase and it can be determined by laser particle size analysis.

In particular, commercially available UPLC chromatography columns comprise stationary phases with a mean (nominal) particle size of 1.7 μm, 1.8 μm, 1.9 μm and 2.1 μm.

For example the Acquity column UPLC BEH $C_{18}$ (1.7 μm×2.1 mm×50 mm) marketed by Waters, whose stationary phase consists of silica particles grafted with end-capped $C_{18}$ groups, is particularly suitable. The cross-linking of the polymer via ethane bridges makes it stable under high pressure. This stationary phase provides for a wide pH range (from 2 to 12).

Chromatography can be conducted using a first solvent for example containing water and formic acid, and a second solvent comprising acetonitrile and formic acid.

Sample Preparation Method

Analysis using ultra-high performance liquid chromatography associated with tandem mass spectrometry (UPLC/MS/MS) can be performed directly i.e. on samples which do not undergo any preliminary treatment apart from filtering. This allows for rapid analysis and the use of a small volume of sample (typically 10 μL).

Alternatively, if it is desired to improve the signal-to-noise ratio and to lower the quantification limit of the tracer compounds, it is advantageous to carry out a preliminary treatment to purify the sample by solid phase extraction. This treatment provides the removal of the salt and organic compounds present in the sample in addition to the tracer compounds.

The use of an extraction support comprising hydrophilic and hydrophobic functions is of particular advantage in this respect. With said support it is effectively possible to perform solid phase extraction in a single step.

A support of macroporous poly(divinylbenzene-co-N-vinylpyrrolidone) copolymer type gives particularly good results for all tracer compounds derived from benzoic acid. It is preferable for the solid phase extraction system to be in the form of a disc rather than a column to avoid risks of plugging by the sample. Oasis® HLB discs marketed by Waters are particularly suitable.

The preparation of the support and the subsequent washing and elution are carried out using mixtures of acetonitrile and water for example, with an increasing pH. A detailed protocol is provided in Example 2 below.

Tracer Compounds

The tracer compounds used for the invention are compounds compatible with fluids naturally present in the deposit, with the oil-bearing rock itself, and with the injected fluids.

The tracer compounds are preferably stealth compounds i.e. they are scarcely absorbed or destroyed by the medium through which they pass. They are also preferably resistant to bacterial contamination at high temperatures and high pressures.

In particular, the tracer compounds may be compounds derived from naphthalene sulphonic acid; preferably they are selected from the derivative compounds of benzoic acid.

In particular, the tracer compounds can be selected from the following fluorinated compounds derived from benzoic acid, that are already known as tracer compounds for hydrocarbon production:
2-fluorobenzoic acid;
3-fluorobenzoic acid;
4-fluorobenzoic acid;
2,3-difluorobenzoic acid;
2,4-difluorobenzoic acid;
2,5-difluorobenzoic acid;
2,6-difluorobenzoic acid;
3,4-difluorobenzoic acid;
3,5-difluorobenzoic acid;
2,3,4-trifluorobenzoic acid;
2,3,6-trifluorobenzoic acid;
2,4,5-trifluorobenzoic acid;
2,4,6-trifluorobenzoic acid;
3,4,5-trifluorobenzoic acid;
2-trifluoromethylbenzoic acid;
3-trifluoromethylbenzoic acid;
4-trifluoromethylbenzoic acid;
3,5-bis(trifluoromethyl)benzoic acid; and
2,3,4,5-tetrafluorobenzoic acid.

These compounds are used as such or in the form of salts, such as sodium or potassium salts.

It is also possible, in addition to or instead of the above compounds, to have recourse to other tracer compounds derived from benzoic acid, meeting the following general formula:

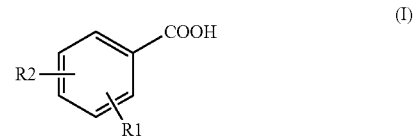

wherein R1 and R2 represent two substituents different from one another selected from F, Cl, Br and CF₃.

Preferably, R1=F and R2=CF₃, or else R1=F and R2=Cl.

The preferred compounds are the following:

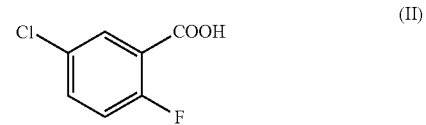

5-chloro-2-fluorobenzoic acid;

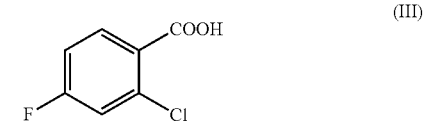

2-chloro-4-fluorobenzoic acid;

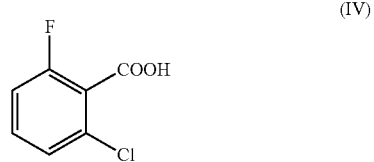

2-chloro-6-fluorobenzoic acid;

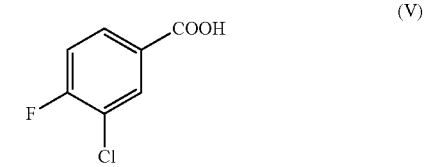

3-chloro-4-fluorobenzoic acid;

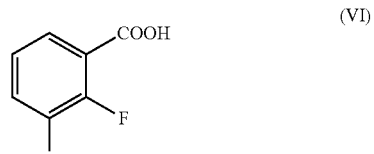

3-chloro-2-fluorobenzoic acid;

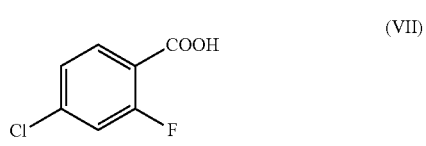

4-chloro-2-fluorobenzoic acid;

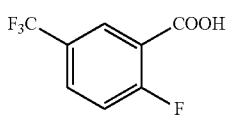

2-fluoro-5-(trifluoromethyl) benzoic acid;

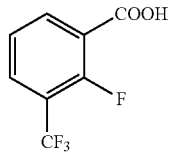

2-fluoro-3-(trifluoromethyl)benzoic acid;

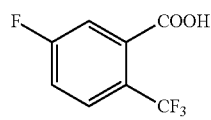

5-fluoro-2-(trifluoromethyl)benzoic acid;

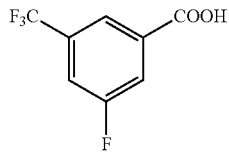

3-fluoro-5-(trifluoromethyl)benzoic acid;

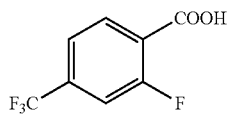

2-fluoro-4-(trifluoromethyl)benzoic acid;

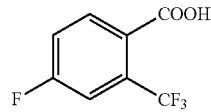

4-fluoro-2-(trifluoromethyl)benzoic acid;

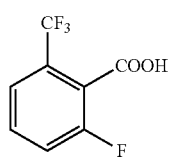

2-fluoro-6-(trifluoromethyl)benzoic acid;

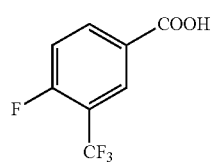

4-fluoro-3-(trifluoromethyl)benzoic acid;

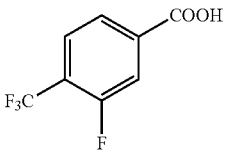

3-fluoro-4-(trifluoromethyl)benzoic acid.

Similarly, these compounds are used as such or in salt form, such as sodium salt or potassium salt.

These compounds are commercially available via suppliers, inter alia, such as Thermo Fisher, Sigma Aldrich, Apollo Scientific . . . .

All the above-mentioned compounds are correctly detected and quantified by means of the method of the invention.

EXAMPLES

The following examples illustrate but do not limit the invention.

Example 1

Analysis without Sample Preparation

Detection assays were conducted for 2-fluoro-5-(trifluoromethyl)benzoic acid (2F-5tFmBA), 5-chloro-2-fluorobenzoic acid (5Cl-2FBA) and also 4-fluorobenzoic acid (4FBA), 2,4-difluorobenzoic acid (2,4dFBA), 3,4,5-trifluorobenzoic acid (3,4,5tFBA), 4-trifluoromethylbenzoic acid (4tFmBA), 2,3,4,5-tetrafluorobenzoic acid (2,3,4,5tetraFBA) and 3,5-bis(trifluoromethyl)benzoic acid (2,5bistFmBA) using UPLC/MS/MS, without any preparation of the samples (except for filtering through 0.2 nm filter). The compounds were dissolved in water derived from a hydrocarbon deposit.

UPLC chromatography was conducted on an Acquity type column UPLC BEH $C_{18}$ (1.7 µm×2.1 mm×50 mm) marketed by Waters. The volume of injected solution was 10 µL. The elution protocol is summarized in following Table 1:

TABLE 1

| elution protocol for UPLC chromatography | | | |
|---|---|---|---|
| Time | Flow rate (mL/min) | Solvent A (ultra-pure water + 0.1% formic acid) | Solvent B (acetonitrile + 0.1% formic acid) |
| 0 min | 0.85 | 95% | 5% |
| 0.2 min | 0.85 | 90% | 10% |
| 1.8 min | 0.85 | 72% | 28% |
| 2.5 min | 0.85 | 20% | 80% |
| 3.2 min | 0.85 | 20% | 80% |
| 4.0 min | 0.85 | 95% | 5% |

The general parameters for tandem mass spectrometry were the following:
- ionisation source (pneumatically- and thermally-assisted electrospray): negative mode;
- capillary voltage: 2.85 kV;
- cone voltage: 22 V;
- extractor potential difference: 2 V;
- RF (hexapole focusing radiofrequency): 0.4 V;
- temperature of source unit: 150° C.;
- desolvation temperature: 450° C.;

flow rate of cone gas (N2) (curtain gas): 30 L/h;
flow rate of desolvation gas (N2): 1000 L/h;
flow rate of collision gas (Ar): 0.1 mL/min. The parameters specific to the different analyzed tracer compounds were the following:
parameters for 2F-5tFmBA: parent ion transition m/z (mass to charge ratio) 207, daughter ion m/z 163, scanning time 0.035 s, cone voltage 19 V, collision energy 12 eV;
parameters for 5Cl-2FBA: parent ion transition m/z 173, daughter ion m/z 129, scanning time 0.035 s, cone voltage 20 V, collision energy 10 eV;
parameters for 4FBA: parent ion transition m/z 138.9, daughter ion m/z 94.9, scanning time 0.035 s, cone voltage 19 V, collision energy 10 eV;
parameters for 2,4dFBA: parent ion transition m/z 156.9, daughter ion m/z 112.9, scanning time 0.035 s, cone voltage 20 V, collision energy 10 eV;
parameters for 3,4,5tFBA: parent ion transition m/z 175, daughter ion m/z 131, scanning time 0.035 s, cone voltage 20 V, collision energy 10 eV;
parameters for 4tFmBA: parent ion transition m/z 188.9, daughter ion m/z 144.9, scanning time 0.035 s, cone voltage 21 V, collision energy 13 eV;
parameters for 2,3,4,5tetraFBA: parent ion transition m/z 193, daughter ion m/z 149, scanning time 0.01 s, cone voltage 24 V, collision energy 12 eV;
parameters for 3,5bistFmBA: parent ion transition m/z 257, daughter ion m/z 213, scanning time 0.01 s, cone voltage 26 V, collision energy 14 eV.

The samples contain the respective tracer compounds at a concentration of $10^{-8}$ g/g. The solution is formed of one volume of production water derived from the oil-bearing deposit, diluted with two volumes of ultra-pure water.

The entire analysis procedure given above can be carried out in about 30 minutes (instead of more than 1 day for gas phase chromatography/mass spectrometry analysis).

It was verified that all the above tracer compounds were correctly detected. In addition, the quantification limit QL was calculated for each tracer compound using the formula $QL=10\times C/(SN)$ where C is the concentration of the tracer compound ($10^{-8}$ g/g) and SN is the signal-to-noise ratio.

The results obtained are summarized in the following Table 2:

TABLE 2 quantification limits of the tracer compounds

| Compound | QL (g/g) |
|---|---|
| 2F-5tFmBA | $1.0 \times 10^{-9}$ |
| 5Cl-2FBA | $2 \times 10^{-9}$ |
| 4FBA | $7.5 \times 10^{-9}$ |
| 2,4dFBA | $9 \times 10^{-9}$ |
| 3,4,5tFBA | $3.5 \times 10^{-9}$ |
| 4tFmBA | $1 \times 10^{-9}$ |
| 2,3,4,5tetraFBA | $2.5 \times 10^{-9}$ |
| 3,5bistFmBA | $1.5 \times 10^{-10}$ |

Example 2

Analysis with Sample Preparation

In this example, the same methodology was followed as in Example 1, but with the addition of preliminary treatment of the sample by solid phase extraction.

This preliminary treatment was performed on a sample of water having a volume of 200 mL. The pH was adjusted to 1.5 with orthophosphoric acid. Solid phase extraction was carried out on an Oasis® HLB disc by Waters. The disc was treated with 5 mL acetonitrile and 10 mL ultra-pure water (pH 1.5). The sample was then poured onto the disc (time of 5 minutes).

Different fractions were then collected:
fraction 1, collected after pouring 5 mL of washing solution containing 10% acetonitrile and 90% ultra-pure water (pH 4.8);
fraction 2, collected after pouring 5 mL of elution solution containing 20% acetonitrile and 80% ultra-pure water (pH 6.8);
fraction 3, collected after pouring 5 mL elution solution containing 35% acetonitrile and 65% ultra-pure water (pH 10);
fractions 4, 5 and 6, collected after pouring three times 5 mL of elution solution containing 80% acetonitrile and 20% ultra-pure water (pH 10).

For optimum recovery of the tracer compounds, the fractions to be kept are fractions 3 to 6 (unless some other tracer compounds are used such as 2,4,6-trifluorobenzoic acid, 2,3,6-trifluorobenzoic acid and 2,6-difluorobenzoic acid, in which case it is appropriate to recover fractions 2 to 6).

The collected fractions 2 and 3 were filtered through 0.2 µm and injected as such for UPLC/MS/MS analysis.

The collected fractions 4, 5 and 6 were filtered through 0.2 µm and diluted in two volumes of ultra-pure water before UPLC/MS/MS analysis.

A first assay was performed with the same production water as in Example 1 and the same concentration of the tracer compound ($10^{-8}$ g/g). This allows the signal-to-noise ratio (SN) obtained to be compared with analysis not including any preliminary treatment of the sample. The results are recorded in Table 3 below:

TABLE 3 comparison of signal-to-noise ratios with and without sample preparation

| Compound | SN without pretreatment | SN with pretreatment (fraction 3) | SN with pretreatment (fraction 4) |
|---|---|---|---|
| 2F-5tFmBA | 170 | 4022 | 1220 |
| 5Cl-2FBA | 97 | 2155 | 1314 |
| 4FBA | 26 | 594 | 496 |
| 2,3,4,5tetraFBA | 83 | 1538 | 351 |
| 3,5bistFmBA | 1254 | 19048 | 23622 |

A second assay was conducted with a lower concentration of tracer compound, namely $5\times10^{-10}$ g/g. It was ascertained that, without preliminary treatment of the sample, the tracer compounds 2F-5tFmBA, 5Cl-2FBA, 4FBA and 2,3,4,5tetraFBA cannot be quantified. With preliminary treatment they can be quantified. Compound 3,5bistFmBA is quantifiable at this concentration even without preliminary preparation.

Example 3

Comparison with GC/MS Detection

In this example, the same methodology as in Example 1 was followed (without preliminary treatment of the sample). The water used was derived from a deposit different from the one used in Examples 1 and 2. At step one the results obtained with the method of the invention were compared with those obtained after GC/MS analysis of a 350 ml sample with preliminary treatment, two solid phase extractions and a derivatization step.

In the same manner as in Example 1, the quantification limit QL was calculated for each tracer compound using the formula QL=10×C/(SN) where C is the concentration of the tracer compound ($10^{-9}$ g/g for GC/MS and $5*10^{-9}$ g/g for UPLC/MS/MS) and SN is the signal-to-noise ratio.

The results are given in Table 4 below:

TABLE 4 comparison of the method of the invention with a GC/MS method

| | GC/MS | | UPLC/MS/MS | |
|---|---|---|---|---|
| Compound | QL (g/g) | QL as a function of actual injected quantity | QL (g/g) | QL as a function of actual injected quantity |
| 4FBA | $1.5 \times 10^{-10}$ | 94 pmol | $5 \times 10^{-9}$ | 1.6 pmol |
| 2,4dFBA | $8 \times 10^{-10}$ | 443 pmol | $6 \times 10^{-9}$ | 1.7 pmol |
| 3,4,5tFBA | $2.5 \times 10^{-10}$ | 124 pmol | $2 \times 10^{-9}$ | 0.5 pmol |
| 4tFmBA | $1.5 \times 10^{-8}$ | 6908 pmol | $8 \times 10^{-10}$ | 0.2 pmol |
| 2,3,4,5tetraFBA | $1.5 \times 10^{-9}$ | 677 pmol | $3 \times 10^{-9}$ | 0.7 pmol |
| 3,5bistFmBA | not detected | — | $2 \times 10^{-10}$ | 0.03 pmol | pmol = $10^{-12}$ mol

At a second step, a sample of production fluid containing 4FBA was taken, derived from an actual tracing campaign.

The concentration of the sample was estimated at $4.9 \times 10^{-9}$ g/g with the GC/MS technique and at $4.6 \times 10^{-9}$ g/g with the UPLC/MS/MS technique: the results therefore tally with each other.

The invention claimed is:

1. Method for surveying a subsurface formation containing hydrocarbons, comprising:
   injecting at least one tracer compound into the subsurface formation;
   recovering a fluid derived from the subsurface formation;
   detecting the tracer compound in the fluid by liquid chromatography analysis coupled with tandem mass spectrometry analysis, the liquid phase chromatography analysis being conducted with a stationary phase composed of particles having a mean size equal to or less than 2.1 µm;
   wherein at least one part of the tracer compound is a compound of formula:

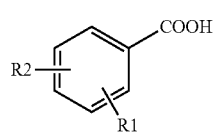

(I)

wherein R1 and R2 represent two substituents different from each other, selected from F and $CF_3$.

2. The method according to claim 1, comprising the injection of a plurality of different tracer compounds into the subsurface formation, the recovery of one or more fluids derived from the subsurface formation and the detection of each tracer compound in the fluid or fluids by liquid chromatography analysis coupled with tandem mass spectrometry analysis, the liquid chromatography analysis being conducted with a stationary phase composed of particles having a mean size equal to or less than 2.1 µm.

3. The method according to claim 1 wherein at least one part of the tracer compound is selected from 2-fluoro-3-(trifluoromethyl)benzoic acid, 2-fluoro-4-(trifluoromethyl)benzoic acid, 2-fluoro-5-(trifluoromethyl)benzoic acid, 2-fluoro-6-(trifluoromethyl)benzoic acid, 3-fluoro-4-(trifluoromethyl)benzoic acid, 3-fluoro-5-(trifluoromethyl)benzoic acid, 4-fluoro-2-(trifluoromethyl)benzoic acid, 4-fluoro-3-(trifluoromethyl)benzoic acid and 5-fluoro-2-(trifluoromethyl)benzoic acid.

4. The method according to claim 1, wherein the tracer compound is injected into the subsurface formation via one or more injection wells, in the form of one or more aqueous solutions, and wherein the fluid or fluids derived from the subsurface formation comprise water and hydrocarbons and are recovered in one or more production wells.

5. The method according to claim 1, wherein the detection of the tracer compound in the fluid comprises:
   taking a sample of fluid;
   optionally treating the fluid sample with solid phase extraction;
   filtering the sample;
   determining the presence or absence of the tracer compound in the sample, and optionally measuring the quantity of the tracer compound present in the sample.

6. The method according to claim 5, wherein the solid phase extraction is conducted on a support having hydrophilic and hydrophobic functions, and preferably on a support of macroporous poly(divinylbenzene-co-N-vinylpyrrolidone) copolymer.

7. The method according to claim 6, wherein the solid phase extraction is performed by treatment of the support with at least one treatment solution, by loading the sample, by washing the support with at least one washing solution and by eluting with at least one elution solution, the treatment, washing and elution solutions preferably being mixtures of acetonitrile and water.

8. Method for surveying a subsurface formation containing hydrocarbons, comprising:
   providing at least one fluid derived from the subsurface formation, the fluid comprising at least one tracer compound injected into the subsurface formation;
   detecting the at least one tracer compound in the fluid by liquid chromatography analysis coupled with tandem mass spectrometry analysis, the liquid phase chromatography analysis being conducted with a stationary phase composed of particles having a mean size equal to or less than 2.1 µm;
   wherein said tracer compound is a compound of formula:

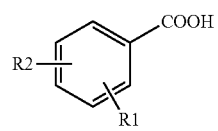

(I)

wherein R1 and R2 represent two groups different from each other, chosen from F and $CF_3$.

9. The method according to claim 8, wherein the at least one fluid comprises a plurality of different said tracer compounds and the detecting comprises detecting each said tracer compound in the at least one fluid by the liquid chromatography analysis coupled with the tandem mass spectrometry analysis, the liquid chromatography analysis being conducted with a stationary phase composed of particles having a mean size equal to or less than 2.1 µm.

10. The method according to claim 8 wherein said tracer compound is selected from 2-fluoro-3-(trifluoromethyl)benzoic acid, 2-fluoro-4-(trifluoromethyl)benzoic acid, 2-fluoro-5-(trifluoromethyl)benzoic acid, 2-fluoro-6-(trifluoromethyl)benzoic acid, 3-fluoro-4-(trifluoromethyl)benzoic acid, 3-fluoro-5-(trifluoromethyl)benzoic acid, 4-fluoro-2-(trifluoromethyl)benzoic acid, 4-fluoro-3-(trifluoromethyl)benzoic acid and 5-fluoro-2-(trifluoromethyl)benzoic acid.

11. The method according to claim 8, comprising injecting said tracer compound into the subsurface formation via one or more injection wells, in the form of one or more aqueous solutions, and wherein the at least one fluid derived from the subsurface formation comprises water and hydrocarbons and is recovered in one or more production wells.

12. The method according to claim 8, wherein the detecting comprises:
   taking a sample of fluid;
   optionally treating the sample with solid phase extraction;
   filtering the sample;
   determining the presence or absence of said tracer compound in the sample, and optionally measuring the quantity of said tracer compound present in the sample.

13. The method according to claim 12, wherein the solid phase extraction is conducted on a support having hydrophilic and hydrophobic functions, and preferably on a support of macroporous poly(divinylbenzene-co-N-vinylpyrrolidone) copolymer.

14. The method according to claim 13, wherein the solid phase extraction is performed by treatment of the support with at least one treatment solution, by loading the sample, by washing the support with at least one washing solution and by eluting with at least one elution solution, the treatment, washing and elution solutions preferably being mixtures of acetonitrile and water.

15. Method for surveying a subsurface formation containing hydrocarbons, comprising:
   injecting at least one tracer compound into the subsurface formation;
   recovering a fluid derived from the subsurface formation;
   detecting the tracer compound in the fluid by liquid chromatography analysis coupled with tandem mass spectrometry analysis, the liquid phase chromatography analysis being conducted with a stationary phase composed of particles having a mean size equal to or less than 2.1 μm, the detecting comprising the following steps:
   taking a sample of fluid;
   treating the sample of fluid with solid phase extraction on a support having hydrophilic and hydrophobic functions;
   filtering the sample; and
   determining the presence or absence of said tracer compound in the sample, and optionally measuring the quantity of said tracer compound present in the sample;
   wherein said tracer compound is a compound of formula:

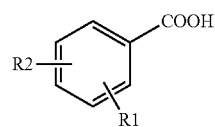

(I)

wherein R1 and R2 represent two groups different from each other, chosen from F and $CF_3$.

16. The method according to claim 15, wherein said support having hydrophilic and hydrophobic functions comprises a support of macroporous poly(divinylbenzene-co-N-vinylpyrrolidone) copolymer.

17. Method for surveying a subsurface formation containing hydrocarbons, comprising:
   providing at least one fluid derived from the subsurface formation, the fluid comprising at least one tracer compound injected into the subsurface formation;
   detecting the at least one tracer compound in the fluid by liquid chromatography analysis coupled with tandem mass spectrometry analysis, the liquid phase chromatography analysis being conducted with a stationary phase composed of particles having a mean size equal to or less than 2.1 μm, the detecting comprising the following steps:
   taking a sample of fluid;
   treating the sample of fluid with solid phase extraction on a support having hydrophilic and hydrophobic functions;
   filtering the sample; and
   determining the presence or absence of said tracer compound in the sample, and optionally measuring the quantity of said tracer compound present in the sample;
   wherein said tracer compound is a compound of formula:

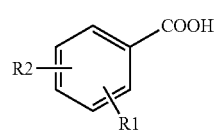

(I)

wherein R1 and R2 represent two groups different from each other, chosen from F and $CF_3$.

18. The method according to claim 17, wherein said support having hydrophilic and hydrophobic functions comprises a support of macroporous poly(divinylbenzene-co-N-vinylpyrrolidone) copolymer.

* * * * *